United States Patent [19]
Nishiyama et al.

[11] Patent Number: 6,103,914
[45] Date of Patent: Aug. 15, 2000

[54] METHOD OF PRODUCING OPTICALLY ACTIVE MATERIAL OF TRICYCLIC COMPOUND

[75] Inventors: Hisao Nishiyama, Aichi; Hiroshi Nagase; Hisanori Wakita, both of Kanagawa, all of Japan

[73] Assignee: Toray Industries, Inc., Japan

[21] Appl. No.: 09/171,499

[22] PCT Filed: Feb. 19, 1998

[86] PCT No.: PCT/JP98/00694

§ 371 Date: Oct. 20, 1998

§ 102(e) Date: Oct. 20, 1998

[87] PCT Pub. No.: WO98/37042

PCT Pub. Date: Aug. 27, 1998

[30] Foreign Application Priority Data

Feb. 21, 1997 [JP] Japan .................................. 9-037253

[51] Int. Cl.[7] ................................................. C07D 307/92
[52] U.S. Cl. ............................................................ 549/458
[58] Field of Search ........................... 549/458, 43, 427

[56] References Cited

U.S. PATENT DOCUMENTS

| | | | |
|---|---|---|---|
| 5,202,447 | 4/1993 | Ohno et al. | 549/458 |
| 5,496,849 | 3/1996 | Ohno et al. | 514/468 |
| 5,716,986 | 2/1998 | Szantay et al. | 514/468 |

FOREIGN PATENT DOCUMENTS 59-161371 of 0000 Japan .
1-279878 11/1989 Japan .

OTHER PUBLICATIONS

Morrison and Boyd, pp. 156–158, 1987.

*Primary Examiner*—Deborah C. Lambkin
*Attorney, Agent, or Firm*—Austin R. Miller

[57] ABSTRACT

Optically active materials of tricyclic compounds, for example, cyclopenta [b] benzofuran derivatives represented by the following formula:

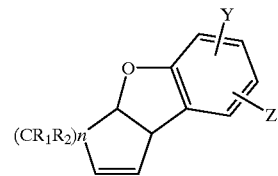

wherein $R_1$, $R_2$, Y and Z independently represent hydrogen, halogen, an alkyl group, or an aryl group; and n represents 0 to 4, are directly produced by adding an optically active alcohol, amine and/or metal salt thereof.

5 Claims, No Drawings

METHOD OF PRODUCING OPTICALLY ACTIVE MATERIAL OF TRICYCLIC COMPOUND

This application is a 371 of PCT/JP58/00694 Feb. 19, 1998.

TECHNICAL FIELD

The present invention relates to a method of producing optically active materials of cyclopenta [b] benzofuran derivatives, e.g., 3a,8b-cis-dihydro-3H-cyclopenta [b] benzofuran used as a raw material for producing 5,6,7-trinor-4,8-inter-m-phenylene $PGI_2$ derivatives useful as medicines, particularly, an anti-thrombogenic agent.

BACKGROUND ART

Optically active materials of derivatives of 3a,8b-cis-dihydro-3H-cyclopenta [b] benzofuran, which is a tricyclic compound, are conventionally synthesized by optical resolution of [7-bromo-3a,8b-cis-dihydro-3H-cyclopenta [b] benzofuran-5-yl] formic acid with an optically active amine, as disclosed in Japanese Unexamined Patent Publication No. 59-161371, or by enzyme reaction thereof, as disclosed in J. Chem. Soc., Chem. Commun., 811, 1995. However, there has been not known yet a simplest direct method of obtaining optically active materials by asymmetric synthesis.

DISCLOSURE OF INVENTION

The optical resolution method using an optically active amine requires a complicated operation comprising forming a complex, and repeatedly carrying out recrystallization, and the enzyme reaction method requires a long reaction time because of a low substrate concentration, and frequently produces results with low reproducibility according to enzyme lots.

In consideration of the above drawbacks of conventional techniques, an object of the present invention is to provide a useful method capable of directly obtaining compounds represented by the following formula (II) using an optically active alcohol or amine:

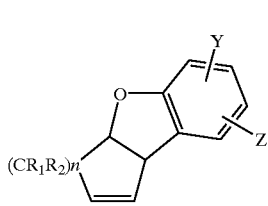

(II)

[wherein $R_1$, $R_2$, Y and Z independently represent hydrogen, halogen, an alkyl group, or an aryl group; and n represents 0 to 4].

In order to achieve the object of the invention, the inventors studied asymmetric induction by cyclization reaction for directly synthesizing 3a,8b-cis-dihyro-3H-cyclopenta [b] benzofuran derivatives as tricyclic compounds. As a result, the intended compounds having high optical purity were found to be obtained, leading to the achievement of the present invention.

The present invention provides a method of producing optically active materials of tricyclic compounds represented by the above formula (II), the method comprising cyclization reaction using an organometallic reagent and compounds represented by the following formula (I):

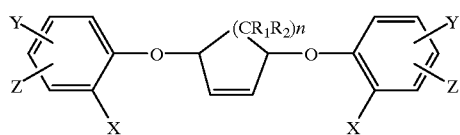

(I)

[wherein X represents halogen; $R_1$, $R_2$, Y and Z independently represent hydrogen, halogen, an alkyl group, or an aryl group; and n represents 0 to 4], wherein in cyclization reaction, an optically active alcohol, amine, or metal salt thereof is added as an additive.

BEST MODE FOR CARRYING OUT THE INVENTION

The present invention has the construction below.

Preferable compounds as the compounds used in the present invention and represented by the above formula (I) are compounds in which X represents chlorine, bromine or iodine; $R_1$, $R_2$, Y and Z independently represent hydrogen, fluorine, chlorine, bromine, iodine, alkyl having 1 to 5 carbon atoms, cycloalkyl having 3 to 8 carbon atoms, cycloalkylalkyl having 4 to 9 carbon atoms, cycloalkenylalkyl having 5 to 10 carbon atoms, aralkyl having 7 to 12 carbon atoms, alkenyl having 2 to 7 carbon atoms, or aryl having 6 to 11 carbon atoms; and n represents 0 to 4. Particularly, 3,5-bis(aryloxy)cyclopentene is preferred, in which X represents chlorine, bromine, or iodine; $R_1$, $R_2$, Y and Z independently represents hydrogen or alkyl having 1 to 5 carbon atoms; and n represents 1. This compound can be produced by condensation reaction of 3,5-dibromocyclopentene and a metal salt of a phenol derivative, as disclosed in Japanese Examined Patent Publication No. 1-31494. However, in the present invention, the method of producing 3,5-bis(aryloxy)cyclopentene is not limited to this method.

In the present invention, the thus-obtained compound represented by the formula (I) is dissolved in an organic solvent, and subjected to cyclization reaction with an organometallic reagent. At this time, an alcohol, an amine and/or a metal salt thereof is added to the reaction system to obtain the intended optically active tricyclic compound represented by formula (II). Examples of the organic solvent used include ether solvents such as diethyl ether, tetrahydrofuran, 1,2-dimethoxyethane, dioxane, and the like. However, tetrahydrofuran is particularly preferred. However, the organic solvent is not limited to these solvents and the organic solvent is generally used in an amount by weight of 1 to 1000 times the weight of the compound represented by formula (I).

Examples of the organometallic reagent used for cyclization reaction include a Grignard's reagent, an organolithium reagent, and the like, but an organolithium reagent is preferably used. Particularly, methyllithium, n-butyllithium, and phenyllithium are used. However, in the present invention, the organometallic reagent is not limited to these reagents. The organometallic reagent is generally used in an amount of 1 to 10 equivalents based on the compound represented by formula (I).

As an optically active alcohol or amine, or a metal salt thereof, binaphthyl derivatives, 2-aminoethanol derivatives and alkaloids are preferably used. Preferred examples of optically active alcohols and amines include (R)-binaphthol, (S)-binaphthol, (R)-2-hydroxy-2'-methoxy-1,1'-binaphthyl, (R)-2-hydroxy-2'-(methoxymethyl)oxy-1,1'-binaphthyl, (R)-2-hydroxy-2'-benzyloxy-1,1'-binaphthyl, (1S,2R)-2-pyrrolidine-1,2-diphenylethanol, (1R,2S)-2-pyrrolidine-1,2-diphenylethanol, cinchonine, cinchonidine, and the like. However, in the present invention, alcohols and amines are not limited to these compounds. As a metal salt, alkali metal salts such as lithium, sodium and potassium salts, and the like are preferably used, but lithium salts are particularly preferable. The alcohol, amine or metal salt thereof is generally used in an amount of 0.001 to 100 equivalents based on the compound represented by formula (I).

In the present invention, the reaction temperature is generally −120 to 100° C., preferably −78 to 30° C. The reaction time is generally 5 minutes to 120 hours, preferably 0.5 to 5 hours. However, in the present invention, the reaction temperature and the reaction time are not limited to these values.

In the present invention, the optically active material represented by formula (II) and obtained by the above reaction is generally isolated by distillation or silica gel column chromatography, but the isolation method is not limited to these methods.

The optically active material represented by formula (II) and obtained by the above reaction has high optical purity, as shown in the examples below. Unlike optical resolution by salt formation, the method of directly producing optically active materials by cyclization reaction according to the present invention requires no complicated operation and is thus very simple. In the present invention, there is no need for enzyme reaction which requires a large amount of solvent and much reaction time, and which exhibits low reproducibility, and thus the method of the present invention can be applied to experimental and industrial production methods.

EXAMPLES

In order to describe the present invention in further detail, reference examples and examples are described.

Reference Example 1
Synthesis of (1R,2S)-2-pyrrolidine-1,2-diphenylethanol represented by the following formula

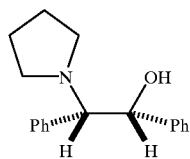

In a 50-mL eggplant type flask with a Y-tube, a Dimroth condenser, and a three-way cock were placed 3.20 g (15 mmol, m.w.=213.28) of (+)-2-amino-1,2-diphenylethanol and 2.77 g (26.09 mmol, m.w.=105.99) of sodium carbonate, followed by deaeration drying and replacement with argon. Next, to the flask were added ethanol (50 mL) and 2.17 mL (16.52 mmol, m.w.=309.9, d=2.35) of 1,4-diiodobutane under a nitrogen stream, followed by heating under reflux at 110° C. for 10 hours. Proceeding of reaction was recognized by TLC (methylene chloride/methanol=5:1, Rf=0.65). Then water (40 mL) was added, and the organic layer was extracted with methylene chloride (40 mL×3), and then dried over anhydrous magnesium sulfate. After filtration and concentration, the residue was isolated and purified by silica gel column chromatography (SiO$_2$=90 g, triethylamine 3 cc, hexane/ether=10:1→1:1) to obtain 3.24 g (12.13 mmol, m.w.=267.0, yield 81%) of white crystals.

$^1$HNMR (270 MHz, CDCl$_3$, TMS): δ 1.83 (m, 4H), 2.66 (m, 4H), 3.29 (d, J=3.4 Hz, 1H), 5.23 (d, J=3.4 Hz, 1H), 6.89–7.13 (m, 10H) ppm.
$^{13}$CNMR (67.8 MHz, CDCl$_3$): δ 23.6, 53.1, 74.1, 77.6, 123.4, 123.9, 126.2, 126.5, 126.8, 127.1, 127.3, 127.5, 127.7, 129.4, 137.6, 140.8 ppm.
IR (KBr) 3478, 3069, 2968, 2799, 2400, 2130, 1645, 1454, 1337, 1196, 1127, 703 cm$^{-1}$
$[\alpha]_D^{22}$ +84.2° (c 0.98, Et$_2$O)
mp.=110° C.
Elementary analysis as C$_{18}$H$_{21}$N$_1$O$_1$ (F.W. 267.370) Calculated value (%) C: 80.86; H: 7.92; N: 5.24. Measured value (%) C: 81.08; H: 7.79; N: 5.00.

Reference Example 2
Synthesis of (1S,2R)-2-pyrrolidine-1,2-diphenylethanol represented by the following formula

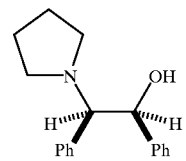

In a 50-mL eggplant type flask with a Y-tube, a Dimroth condenser, and a three-way cock were placed 2.13 g (10 mmol, m.w.=213.28) of (−)-2-amino-1,2-diphenylethanol and 1.85 g (17.39 mmol, m.w.=105.99) of sodium carbonate, followed by deaeration drying and replacement with argon. Next, to the flask were added ethanol (50 mL) and 1.45 mL (11.01 mmol, m.w.=309.9, d=2.35) of 1,4-diiodobutane under a nitrogen stream, followed by heating under reflux at 110° C. for 10 hours. Proceeding of reaction was recognized by TLC (methylene chloride/methanol=5:1, Rf=0.65). Then water (20 mL) was added, and the organic layer was extracted with methylene chloride (30 mL×3), and then dried over anhydrous magnesium sulfate. After filtration and concentration, the residue was isolated and purified by silica gel column chromatography (SiO$_2$=60 g, triethylamine 2 cc, hexane/ether=10:1→1:1) to obtain 1.86 g (6.97 mmol, m.w.=267.0, yield 70%) of white crystals.

$_1$HNMR (270 MHz, CDCl$_3$, TMS): δ 1.83 (m, 4H), 2.66 (m, 4H), 3.29 (d, J=3.4 Hz, 1H), 5.23 (d, J=3.4 Hz, 1H), 6.89–7.13 (m, 10H) ppm.

Reference Example 3
Synthesis of (R)-2-hydroxy-2'-methoxy-1,1'-binaphthyl represented by the following formula

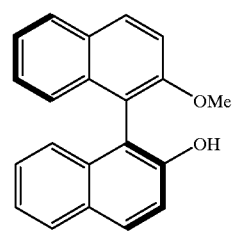

To a 200-mL eggplant type flask were added 5.15 g (18 mmol, m.w.=286.33) of (R)-1,1'-binaphthol and 7.46 g (54 mmol, m.w.=138.21) of potassium carbonate, followed by deaeration drying and replacement with argon. Next, the mixture was dissolved in acetone (90 mL) under a nitrogen stream, and 1.72 mL (18 mmol, m.w.=126.13, d=1.332) of dimethylsulfuric acid was added dropwise to the resultant solution, followed by stirring at room temperature for 13.5 hours. Proceeding of reaction was recognized by TLC (hexane, Rf=0.44). Then, after filtration with a Florisil/celite layer and concentration, the residue was isolated and purified by silica gel column chromatography (SiO$_2$=125 g, development solvent: benzene) to obtain 3.80 g (12.6 mmol, m.w.=300.4, yield 70%) of white powder.

$^1$HNMR (270 MHz, CDCl$_3$, TMS): δ 3.81 (s, 1H), 4.91 (s, 1H), 7.04 (d, J=8.8 Hz, 1H), 7.15–7.40 (m, 6H), 7.49 (d, J=8.8 Hz, 1H), 7.86–7.92 (m, 3H), 8.06 (d, J=9.3 Hz, 1H) ppm.

$^{13}$CNMR (67.9 MHz, CDCl$_3$): δ 56.6, 113.8, 115.0, 115.3, 117.4, 123.2, 124.2, 124.8, 124.9, 126.4, 127.3, 128.1, 129.1, 129.4, 129.8, 131.0, 133.7, 134.0, 140.9, 151.2, 156.0 ppm.

IR (KBr)-3520, 3054, 1604, 1506, 1263, 1079, 816, 749 cm$^{-1}$ $[α]_D^{21}$ +39.2° (c 1.00, Et$_2$O)

mp.=113° C.

Elementary analysis as C$_{21}$H$_{16}$O$_2$ (F.W. 300.356) Calculated value (%) C: 83.98; H: 5.37. Measured value (%) C: 83.69; H: 5.20.

Reference Example 4

Synthesis of (R)-2-hydroxy-2'-methoxymethyloxy-1,1'-binaphthyl represented by the following formula

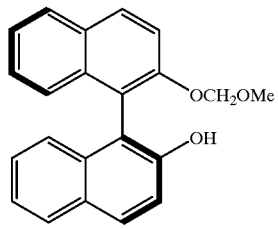

To a 100-mL eggplant type flask was added 2.864 g (10 mmol, m.w.=286.33) of (R)-1,1'-binaphthol, followed by deaeration drying and replacement with argon. Next, the mixture was dissolved in methylene chloride (60 mL) under a nitrogen stream, and 3.83 mL (22 mmol, m.w.=129.25, d=0.742) of diisopropylethylamine was added to the resultant solution. To the solution was added dropwise 0.84 mL (11 mmol, m.w.=80.51, d=1.068) of chloromethyl ether under ice cooling, followed by stirring at room temperature for 2.5 hours. Proceeding of reaction was recognized by TLC (methylene chloride/hexane/ether=9:5:1, Rf=0.56). Then, to the reaction solution was added 1N hydrochloric acid (22 mL) under ice cooling, followed by extraction with methylene chloride (50 mL×3) and drying over sodium sulfate. After filtration and concentration, the residue was isolated and purified by silica gel column chromatography (SiO$_2$=100 g, methylene chloride/hexane/ether=3:5:0.4) to obtain 2.475 g (7.49 mmol, m.w.=330.38, yield 75%) of white powder.

$^1$HNMR (270 MHz, CDCl$_3$, TMS): δ 3.18 (s, 3H), 4.79 (s, 1H), 5.08 (q, J=7.8, 6.8 Hz, 2H), 7.07 (d, J=8.3 Hz, 1H), 7.20–7.41 (m, 6H), 7.60 (d, J=9.3 Hz, 1H), 7.85–7.93 (m, 3H), 8.03 (d, J=9.3 Hz, 1H) ppm.

$^{13}$CNMR (67.8 MHz, CDCl$_3$): δ 56.1, 95.0, 115.1, 117.1, 117.5, 117.6, 123.3, 124.7, 124.8, 125.1, 126.5, 127.2, 128.0, 128.1, 129.1, 129.8, 130.2, 130.9, 133.8, 133.9, 151.2, 153.7 ppm.

IR (KBr) 3517, 3054, 1619, 1592, 1507, 1468, 1374, 1238, 1204, 1147, 1074, 906, 814, 750 cm$^{-1}$ $[α]_D^{21}$ +51.3° (c 0.99, Et$_2$O)

mp.=110° C.

Elementary analysis as C$_{22}$H$_{18}$O$_3$ (F.W. 330.382) Calculated value (%) C: 79.98; H: 5.49. Measured value (%) C: 80.30; H: 5.47.

Reference Example 5

Synthesis of (R)-2-hydroxy-2'-(tert-butyldimethylsilyl)oxy-1,1'-binaphthyl represented by the following formula

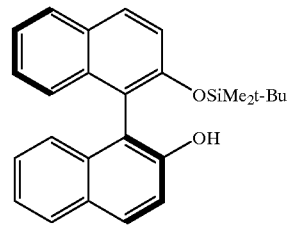

To a 100-mL eggplant type flask were added 1.432 g (5 mmol, m.w.=286.33) of (R)-1,1'-binaphthol and 1.021 g (15 mmol, m.w.=68.08) of imidazole, followed by deaeration drying and replacement with argon. Next, the mixture was dissolved in N,N-dimethylformamide (30 mL) under a nitrogen stream, and 904.3 mg (6 mmol, m.w.=150.72) of tert-butyldimethylchlorosilane dissolved in N,N-dimethylformamide (30 mL) was added dropwise to the resultant solution, followed by stirring at room temperature for 24 hours. Proceeding of reaction was recognized by TLC (methylene chloride/hexane/ether =3:5:0.1, Rf=0.43). Then, after concentration, the residue was isolated and purified by silica gel column chromatography (SiO$_2$=75 g, methylene chloride/hexane/ether =5:5:0.5) to obtain 1.794 g (4.48 mmol, m.w.=400.19, yield 90%) of white powder.

$^1$HNMR (270 MHz, CDCl$_3$): δ −0.21 (s, 3H), 0.00 (s, 3H), 0.52 (s, 3H), 7.08 (d, J=8.6 Hz, 1H), 7.18-7.39 (m, 7H), 7.81–7.95 (m, 4H) ppm.

$^{13}$CNMR (67.8 MHz, CDCl$_3$): δ −4.7, −4.4, 17.6, 25.0, 115.5, 117.5, 118.3, 121.2, 123.1, 124.2, 125.2, 126.2, 127.0, 127.9, 128.1, 128.6, 129.1, 129.5, 129.7, 130.5, 133.8, 134.2, 151.4, 152.3 ppm.

IR (KBr) 3510, 3058, 2494, 1903, 1593, 1508, 1467, 1312, 1254, 1207, 1148, 1074, 998, 781, 748 cm$^{-1}$ $[α]_D^{22}$ +20.9° (c 0.94, Et$_2$O)

mp.=53° C.

Elementary analysis as C$_{26}$H$_{27}$O$_2$Si$_1$ (F.W. 399.59) Calculated value (%) C: 78.15; H: 6.81. Measured value (%) C: 78.52; H: 7.07.

Reference Example 6

Synthesis of (R)-2-hydroxy-2-benzyloxy-1,1'-binaphthyl represented by the following formula

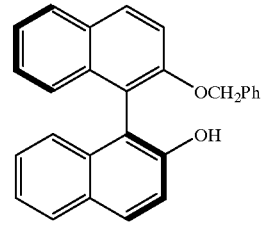

To a 50-mL eggplant type flask was added 987 mg (2.46 mmol, m.w.=400.59) of (R)-2-hydroxy-2'-(dimethyl-tert-butylsilyl)oxy-1,1'-binaphthyl, followed by deaeration drying and replacement with argon. Next, the mixture was dissolved in THF (20 mL) under a nitrogen stream, 236.6 mg (9.86 mmol, m.w.=24.0) of sodium hydride dissolved in THF (10 mL) was added to the resultant solution, and 0.439 mL (3.69 mmol, m.w.=171.04, d=1.438) of benzyl bromide was added dropwise to the solution, followed by stirring at 50° C. for 19 hours. Proceeding of reaction was recognized by TLC (hexane/ethyl acetate=10:1, Rf=0.50). Then, after concentration, brine (20 mL) was added to the residue, followed by extraction with methylene chloride (20 mL×3) and drying over $Na_2SO_4$. After concentration, the residue was isolated and purified by silica gel column chromatography ($SiO_2$=70 g, hexane/ethyl acetate=100:1) to obtain 444 mg (0.90 mmol, m.w.=491.09, yield 37%) of white powder. To a 30-mL of eggplant type flask was added 425 mg (0.87 mmol, m.w.=491.09) of the powder, followed by deaeration drying and replacement with argon. Next, the mixture was dissolved in THF (10 mL) under a nitrogen stream, and 1.04 mL (1.04 mmol, 1 mol/l THF solution) of tetra-n-butylammonium fluoride was added to the resultant solution, followed by stirring at room temperature for 6 hours. Proceeding of reaction was recognized by TLC (benzene, Rf=0.43). Then, after concentration, an aqueous $NH_4Cl$ solution (10 mL) was added to the residue, followed by extraction with methylene chloride (10 mL×2) and drying over $Na_2SO_4$. After filtration and concentration, the residue was isolated and purified by silica gel column chromatography ($SiO_2$=30 g, benzene) to obtain 210 mg (0.56 mmol, m.w.=376.45, yield 56%) of white powder.

$^1$HNMR (270 MHz, $CDCl_3$, TMS): δ 4.93 (s, 1H), 5.09 (d, J=3.4 Hz, 2H), 7.01–7.40 (m, 12H), 7.45 (d, J=8.8 Hz, 1H), 7.86–8.99 (m, 4H) ppm.

$^{13}$CNMR (67.9 MHz, $CDCl_3$): δ 71.1, 115.1, 116.0, 116.8, 117.5, 123.2, 123.8, 124.4, 124.9, 125.0, 126.4, 126.9, 127.3, 127.6, 128.1, 128.3, 129.1, 129.7, 129.8, 130.8, 133.8, 134.1, 136.9, 151.3, 155.0 ppm.

IR (KBr) 3503, 3057, 1619, 1592, 1508, 1463, 1378, 1333, 1267, 1213, 1173, 1141, 1081, 1020, 970, 812, 744 $cm^{-1}$ $[\alpha]_D^{22}$ +79.7° (c 0.35, $Et_2O$)

mp.=56° C.

Elementary analysis as $C_{17}H_{20}O_2$ ($H_2O$) (F.W. 394.469) Calculated value (%) C: 82.21; H: 5.62. Measured value (%) C: 82.57; H: 5.71.

Example 1
Asymmetric cyclization using (R)-1,1'-binaphthol

In double Schlenk's tubes with a three-way cock, 410 mg (1 mmol, m.w.=410.0, white solid) of bis(o-bromophenoxy) cyclopentene was placed in one of the tubes, and 314.9 mg (1.2 mmol, m.w.=286.33) of (R)-1,1'-binaphthol was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 1.60 mL (2.42 mmol, 1.51N hexane solution) and 1.46 mL (2.20 mmol, 1.51N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography ($SiO_2$=10 g, hexane) to obtain 118 mg (0.75 mmol, m.w.=158.2, yield 75%) of cyclized product as an oily substance. The optical yield of the cyclized product was determined to 26% ee by using chiral gas chromatography (chiraldex G-TA 30 m, colm. temp.=110° C., inj. temp.=135° C., det. temp.=135° C., He=1.5 atm).

Example 2
Asymmetric cyclization using (R)-2-hydroxy-2'-methoxy-1, 1'-binaphthyl In double Schlenk's tubes with a three-way cock, 410 mg (1 mmol, m.w.=410.0, white solid) of bis(o-bromophenoxy) cyclopentene was placed in one of the tubes, and 360.5 mg (1.2 mmol, m.w.=300.4) of (R)-2-hydroxy-2'-methoxy-1,1'-binaphthyl was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.88 mL (1.32 mmol, 1.51N hexane solution) and 1.46 mL (2.20 mmol, 1.51N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography ($SiO_2$=10 g, hexane) to obtain 115 mg (0.73 mmol, m.w.=158.2, yield 73%) of cyclized product as an oily substance. 336 mg (1.2 mmol, m.w.=300.4, recovery yield 93%) of ligand was recovered by a development solvent of hexane/ether=1:1 from the after fraction of the column. The optical yield of the cyclized product was determined to 87% ee by using chiral gas chromatography (chiraldex G-TA 30 m, colm. temp.=110° C., inj. temp.=135° C., det. temp.=135° C., He=1.5 atm).

$^1$HNMR (270 MHz, $CDCl_3$, TMS): δ 2.80 (dd, J=2.0, 1.5 Hz, 1H), 2.87 (dd, J=6.1, 1.5 Hz, 1H), 4.37 (d, J=8.7 Hz, 1H), 5.43 (m, 1H), 5.76 (s, 1H), 6.73–7.21 (m, 4H) ppm.

$[\alpha]_D^{21}$ −207.2° (c 0.86, $Et_2O$)

Example 3
Asymmetric cyclization using (R)-2-hydroxy-2'-methoxymethyloxy-1,1'-binaphthyl In double Schlenk's tubes with a three-way cock, 410 mg (1 mmol, m.w.=410.0, white solid) of bis(o-bromophenoxy) cyclopentene was placed in one of the tubes, and 396.5 mg (1.2 mmol, m.w.=330.4) of (R)-2-hydroxy-2'-methoxymethyloxy-1,1'-binaphthyl was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.88 mL (1.32 mmol, 1.51N hexane solution) and 1.46 mL (2.20 mmol, 1.51N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether=10:1, Rf =0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 128 mg (0.81 mmol, m.w.=158.2, yield 81%) of cyclized product as an oily substance. 381 mg (1.15 mmol, m.w.=330.4, recovery yield 96%) of ligand was recovered by a development solvent of hexane/ether=1:1 from the after fraction of the column. The optical yield of the cyclized product was determined to 81% ee by using chiral gas chromatography (chiraldex G-TA 30 m, colm. temp.=110° C., inj. temp.=135° C., det. temp.=135° C., He=1.5 atm).

Example 4

Asymmetric cyclization using (R)-2-hydroxy-2'-(tert-butyldimethylsilyl)oxy-1,1'-binaphthyl In double Schlenk's tubes with a three-way cock, 410 mg (1 mmol, m.w.=410.0, white solid) of bis(o-bromophenoxy) cyclopentene was placed in one of the tubes, and 480.7 mg (1.2 mmol, m.w.=400.6) of (R)-2-hydroxy-2'-(tert-butyldimethylsilyl)oxy-1,1'-binaphthyl was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.88 mL (1.32 mmol, 1.51N hexane solution) and 1.46 mL (2.20 mmol, 1.51N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 291 mg (0.591 mmol, m.w.=158.2, yield 59%) of cyclized product as an oily substance. 470.3 mg (1.17 mmol, m.w.=400.6, recovery yield 98%) of ligand was recovered by a development solvent of hexane/ether=1:1 from the after fraction of the column. The optical yield of the cyclized product was determined to 3% ee by using chiral gas chromatography (chiraldex G-TA 30 m, colm. temp.=110° C., inj. temp.=135° C., det. temp.=135° C., He=1.5 atm).

Example 5

Asymmetric cyclization using (R)-2-hydroxy-2'-benzyloxy-1,1'-binaphthyl

In double Schlenk's tubes with a three-way cock, 410 mg (1 mmol, m.w.=410.0, white solid) of bis(o-bromophenoxy) cyclopentene was placed in one of the tubes, and 451.7 mg (1.2 mmol, m.w.=376.5) of (R)-2-hydroxy-2'-benzyloxy-1,1'-binaphthyl was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.88 mL (1.32 mmol, 1.51N hexane solution) and 1.46 mL (2.20 mmol, 1.51N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether 10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 126.8 mg (0.80 mmol, m.w.=158.2, yield 80%) of cyclized product as an oily substance. 440.1 mg (1.17 mmol, m.w.=376.5, recovery yield 97%) of ligand was recovered by a development solvent of hexane/ether=1:1 from the after fraction of the column. The optical yield of the cyclized product was determined to 80% ee by using chiral gas chromatography (chiraldex G-TA 30 m, colm. temp.=110° C., inj. temp.=135° C., det. temp.=135° C., He=1.5 atm).

Example 6

Asymmetric cyclization using (1S,2R)-2-pyrrolidine-1,2-diphenylethanol

In double Schlenk's tubes with a three-way cock, 410 mg (1 mmol, m.w.=410.0, white solid) of bis(o-bromophenoxy) cyclopentene was placed in one of the tubes, and 320.4 mg (1.2 mmol, m.w.=267.0) of (1S,2R)-2-pyrrolidine-1,2-diphenylethanol was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.87 mL (1.32 mmol, 1.52N hexane solution) and 1.45 mL (2.20 mmol, 1.52N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 109.1 mg (0.69 mmol, m.w.=158.2, yield 69%) of cyclized product as an oily substance. 292.4 mg (1.10 mmol, m.w.=267.0, recovery yield 92%) of ligand was recovered by a development solvent of hexane/ether=1:1 from the after fraction of the column. The optical yield of the cyclized product was determined to 71% ee by using chiral gas chromatography (chiraldex G-TA 30 m, colm. temp.=110° C., inj. temp.=135° C., det. temp.=135° C., He=1.5 atm).

Example 7

Asymmetric cyclization using (1R,2S)-2-pyrrolidine-1,2-diphenylethanol

In double Schlenk's tubes with a three-way cock, 410 mg (1 mmol, m.w.=410.0, white solid) of bis(o-bromophenoxy) cyclopentene was placed in one of the tubes, and 320.4 mg (1.2 mmol, m.w.=267.0) of (1R,2S)-2-pyrrolidine-1,2-diphenylethanol was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.87 mL (1.32 mmol, 1.52N hexane solution) and 1.4S mL (2.20 mmol, 1.52N hexane solution) of n-BuLi were slowly added to the ligand side and the substrate side, respectively. The ligand side and the substrate side were mixed and stirred at the temperature hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 117 mg (0.74 mmol, m.w.=158.2, yield 74%) of cyclized product as an oily substance. 300 mg (1.12 mmol, m.w.=267.0, recovery yield 94%) of ligand was recovered by a development solvent of hexane/ether=1:1 from the after fraction of the column. The optical yield of the cyclized product was determined to 42% ee by using chiral gas chromatography (chiraldex G-TA 30 m, colm. temp.=110° C., inj. temp.=135° C., det. temp.=135° C., He=1.5 atm).

Example 8
Asymmetric cyclization using cinchonidine

In double Schlenk's tubes with a three-way cock, 410 mg (1 mmol, m.w.=410.0, white solid) of bis(o-bromophenoxy) cyclopentene was placed in one of the tubes, and 353.3 mg (1.2 mmol, m.w.=294.4) of cinchonidine was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.87 mL (1.32 mmol, 1.52N hexane solution) and 1.45 mL (2.20 mmol, 1.52N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 297.1 mg (0.61 mmol, m.w.=158.2, yield 61%) of cyclized product as an oily substance. The optical yield of the cyclized product was determined to 58% ee by using chiral gas chromatography (chiraldex G-TA 30 m, colm. temp.=110° C., inj. temp.=135° C., det. temp.=135° C., He=1.5 atm).

Example 9
Asymmetric cyclization using cinchonine

In double Schlenk's tubes with a three-way cock, 410 mg (1 mmol, m.w.=410.0, white solid) of bis(o-bromophenoxy) cyclopentene was placed in one of the tubes, and 353.3 mg (1.2 mmol, m.w.=294.4) of cinchonine was placed in the other tube, followed by deaeration drying and replacement with argon. To each of the tubes was added THF (3 mL×2) under a nitrogen stream, followed by stirring at room temperature. Next, the temperature was kept at −73° C. (dry ice/acetone bath) or less, and 0.87 mL (1.32 mmol, 1.52N hexane solution) and 1.45 mL (2.20 mmol, 1.52N hexane solution) of n-BuLi were slowly added to the ligand side and the substrate side, respectively. The ligand side and the substrate side were mixed and stirred at the temperature kept low. Then, the temperature was raised to 0° C. over 1.5 hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 117.4 mg (0.74 mmol, m.w.=158.2, yield 74%) of cyclized product as an oily substance. The optical yield of the cyclized product was determined to 56% ee by using chiral gas chromatography (chiraldex G-TA 30 m, colm. temp.=110° C., inj. temp.=135° C., det. temp.=135° C., He=1.5 atm).

Example 10
Asymmetric cyclization using sparteine

In a Schlenk's tube was placed 0.28 mL (1.2 mmol, m.w.=234.4, d=1.02) of sparteine, followed by deaeration drying and replacement with argon. To the tube was added THF (5 mL) under a nitrogen stream, followed by stirring at room temperature. Next, the temperature was kept at −73° C. (dry ice/acetone bath) or less, and 1.46 mL (2.20 mmol, 1.51N hexane solution) of n-BuLi was slowly added to the tube. to the mixture was added 410 mg (1 mmol, m.w.=410.0, white solid) of bromophenoxycyclopentene at the temperature kept low, and the resultant mixture was stirred. Then, the temperature was raised to 0° C. over 1.5 hours (10° C. rise in temperature for about 13 min.). Proceeding of reaction was recognized by TLC (hexane/ether=10:1, Rf=0.58, Merck 5715). To the reaction solution was added 10 mL of water to stop reaction, and extraction with ether (10 mL×2) was carried out. The organic layer was then dried over anhydrous sodium sulfate. After filtration and concentration, the residue was purified by silica gel column chromatography (SiO$_2$=10 g, hexane) to obtain 117 mg (0.74 mmol, m.w.=158.2, yield 74%) of cyclized product as an oily substance. The optical yield of the cyclized product was determined to 2% ee by using chiral gas chromatography (chiraldex G-TA 30 m, colm. temp.=110° C., inj. temp.=135° C., det. temp.=135° C., He=1.5 atm).

Industrial Applicability

As described above, the present invention can produce optically active materials of tricyclic compounds with high purity by adding optically active alcohol, amine or a metal salt thereof. The production method of the present invention requires neither complicated optical resolution operation nor enzyme reaction requiring a large amount of solvent and much time for reaction and exhibiting low reproducibility, can be applied to experimental and industrial production methods, and is thus very advantageous.

What is claimed is:
1. A method of producing an optically active material of a tricyclic compound represented by the following formula (II):

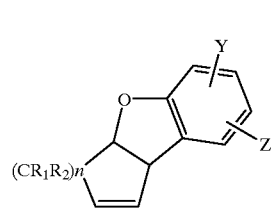

wherein R$_1$, R$_2$, Y and Z independently represent hydrogen, halogen, an alkyl group, or an aryl group; and n represents 0 to 4, wherein in cyclization reaction using an organometallic reagent and a compound represented by the following formula (I), an optically active alcohol, amine, or metal salt thereof is added as an additive;

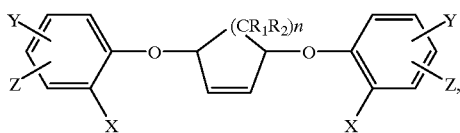 (I)

wherein X represents halogen; $R_1$, $R_2$, Y and Z independently represent hydrogen, halogen, an alkyl group, or an aryl group; and n represents 0 to 4.

2. The method of producing an optically active material of a tricyclic compound according to claim 1, wherein the compound represented by the formula (I) is 3,5-bis(aryloxy) cyclopentene in which n is 1.

3. The method of producing an optically active material of tricyclic compound according to claim 1 or 2, wherein the organometallic reagent is organolithium.

4. The method of producing an optically active material of tricyclic compound according to claim 1 or 2, wherein the additive is a metal salt of an optically active alcohol.

5. The method of producing an optically active material of a tricyclic compound according to claim 1 or 2, wherein the organometallic reagent is organolithium, and the additive is a metal salt of an optically active alcohol.

* * * * *

UNITED STATES PATENT AND TRADEMARK OFFICE
CERTIFICATE OF CORRECTION

PATENT NO. : 6,103,914
DATED : August 15, 2000
INVENTOR(S) : Hisao Nishiyama, Hiroshi Nagase and Hisanori Wakita It is certified that error appears in the above-indentified patent and that said Letters Patent is hereby corrected as shown below:

Column 10, line 60, please change "1.4S" to --1.45--.

Signed and Sealed this

Twenty-fourth Day of April, 2001

Attest:

NICHOLAS P. GODICI

Attesting Officer

Acting Director of the United States Patent and Trademark Office